United States Patent [19]
Amiche

[11] Patent Number: 6,132,773
[45] Date of Patent: Oct. 17, 2000

[54] METHOD FOR PREPARING PARTICLES COMPRISING A CORE AND A SILICA SHELL

[75] Inventor: Frédéric Amiche, Vaucresson, France

[73] Assignee: Rhodia Chimie, Courbevoie, France

[21] Appl. No.: 09/171,493

[22] PCT Filed: Apr. 22, 1997

[86] PCT No.: PCT/FR97/00720

§ 371 Date: Oct. 20, 1998

§ 102(e) Date: Oct. 20, 1998

[87] PCT Pub. No.: WO97/40106

PCT Pub. Date: Oct. 30, 1997

[30] Foreign Application Priority Data

Apr. 22, 1996 [FR] France ................................ 96 05134

[51] Int. Cl.⁷ .............................. A01N 25/34; A61K 9/14; A61K 9/16
[52] U.S. Cl. ......................... 424/490; 424/403; 424/489; 428/402.24
[58] Field of Search ..................................... 424/489, 490; 428/402.24

[56] References Cited

U.S. PATENT DOCUMENTS 2,885,366  5/1959  Iler ............................................ 252/313
5,628,932  5/1997  Linton ....................................... 252/518

Primary Examiner—Thurman K. Page
Assistant Examiner—Susan Tran
Attorney, Agent, or Firm—Jean-Louis Seugnet

[57] ABSTRACT

The invention discloses a method for preparing particles comprising a dense silica shell and a core of another material, through rapid precipitation of active silica from a an aqueous alkaline metal silicate solution with pH adjustment by means of an acidifying agent, on a material support other than silica, separation of the silica slurry formed and drying of the recovered silica suspension. These composite particles consisting of a shell formed of dense silica and a non-polymer organic material core with biological, in particular phytosanitary, activity can be used for the slow release of the said solid non-polymer organic material with biological, in particular phytosanitary, activity, by slow diffusion through the silica shell.

**26 Cla

METHOD FOR PREPARING PARTICLES COMPRISING A CORE AND A SILICA SHELL

This application is an application under 35 U.S.C. Section 371 of International Application Number PCT/FR97/00720, filed on Apr. 22, 1997.

The subject-matter of the present invention is a method for preparing particles comprising a dense silica shell and a core composed of a support made of a material other than silica by precipitation on the said core of active silica from an aqueous alkali metal silicate solution. Another subject-matter of the invention, as novel industrial products, is composite particles composed of a shell formed of dense silica and of a core made of a non-polymer organic material possessing biological activity. The particles obtained according to the method of the invention can be used as fillers for rubber, polymers, concretes or papers or as vehicles for solid active materials or active principles, in particular possessing biological activity, constituting the core or included in the core, with fast or slow release of the active material or of the active principle by destruction of the shell by mechanical or chemical action or by diffusion.

It is known to prepare heterogeneous particles composed of a dense silica shell deposited on a core composed of a charge other than silica by slow precipitation of active silica on the said core from an aqueous alkali metal silicate solution, with adjustment of the pH using an acid (U.S. Pat. No. 2,885,366). According to this document, the precipitation operation can be carried out in a medium of low ionic strength with a rate of addition of silicate lower than a certain parameter S (expressed as weight of silica to be added per hour with respect to the weight of core to be coated) defined by the following equation $$S = (A/200)2^n$$

n being equal to (T-90)/10

A representing the specific surface, expressed in $m^2/g$, of the support to be coated and T the temperature in ° C., on pain of seeing the formation of nuclei of dense particles of silica.

For this reason, the operation of precipitating the active silica is lengthy; thus, the deposition of the order of 20 parts by weight of silica on 100 parts by weight of calcium carbonate at a temperature of the order of 80 to 90° C. requires a precipitation reaction lasting between 3 and 5 hours.

The Inventor has found a novel method which makes it possible rapidly to precipitate dense active silica on a core composed of a charge other than silica, without the risk of formation of nuclei of silica particles.

In a simplified way, "dense" is understood to mean a silica shell formed of a continuous layer composed of a silica lattice, in contrast to a layer composed of a porous assembly of individual silica particles.

The present invention thus consists of a method for preparing particles comprising a dense silica shell by precipitation of active silica from an aqueous alkali metal M silicate solution, with an $SiO_2/Na_2O$ ratio of at least 2, preferably of the order of 2.5 to 4, with adjustment of the pH using an acidifying agent, on a support made of a material other than silica, separation of the silica slurry formed and drying of the silica suspension recovered, the said method being characterized in that the operation of formation of silica slurry by precipitation is carried out according to the following stages:

a first stage consisting in employing an initial vessel heel with a pH of the order of 8 to 10 comprising water, at least one organic or inorganic support other than silica which is insoluble in water under the pH and temperature conditions of the slurry formation operation, an electrolyte salt from the group of alkali metals, the amount of electrolyte present being at least approximately 0.4 mol, preferably of the order of 0.4 to 1.5 mol, of alkali metal ion per litre of vessel heel, and optionally a buffer or basic agent, at a temperature of the order of 80 to 98° C.;

a second stage consisting in introducing, into the said vessel heel, the alkali metal silicate in the form of an aqueous solution containing at least approximately 100 grams of $SiO_2$/litre, preferably of the order of 100 to 330 grams of $SiO_2$/litre, and the acidifying agent, under conditions such that the kinetics K of formation of active silica, expressed in grams of silica/hour/gram of support, corresponds to a value $$K \geq 3(A/200)2^n,$$

preferably $K \geq 4(A/200)2^n$ and very particularly $K \geq 6(A/200)2^n$ n being equal to (T-90)/10

A representing the specific surface, expressed in $m^2/g$, of the support to be coated and T the temperature in ° C., the reaction mixture exhibiting a substantially constant pH of the order of 8 to 10 and being maintained at a temperature of the order of 80 to 98° C., until the desired amount of active silica has been formed.

The choice of the silicate and of the acidifying agent for carrying out the method of the invention is made in a way well known per se.

The alkali metal silicate is advantageously a sodium or potassium silicate.

Mention may very particularly be made of sodium silicates.

Use is generally made, as acidifying agent, of an inorganic acid, such as sulphuric acid, nitric acid or hydrochloric acid, or an organic acid, such as acetic acid, formic acid or carbonic acid. It is preferably sulphuric acid. The latter can be employed in the dilute or concentrate form, preferably in the form of an aqueous solution exhibiting a concentration of the order of 60 to 400 g/l. If it is carbonic acid, the latter can be introduced in the gaseous form.

Mention may be made, among the materials which can constitute the support for the implementation of the method of the invention, of any solid or liquid, inorganic or organic, compound of any shape (spherical, acicular, and the like) which is inert with respect to active silica (hydroxylated silica) and which is insoluble in water under the pH and temperature conditions of the slurry formation operation. The said material is preferably in solid form.

"Compound which is inert with respect to silica" is understood to mean any compound which remains stable under the conditions for precipitation of silica.

"Compound which is insoluble in water" is understood to mean any compound exhibiting a solubility in water of less than approximately 0.5% by weight at 25° C.

Mention may be made, as example of materials, of:

solid inorganic metal salts, such as calcium carbonate, zirconium carbonate, barium carbonate, lead carbonate, zinc sulphide, silver chloride, barium sulphate, aluminium phosphate, titanium phosphate, and the like, metal powders, such as iron, nickel, aluminium or copper powders, and the like, solid metal oxides or hydroxides, such as aluminium, chromium, iron, titanium, zirconium, zinc, titanium or cobalt oxides, nickel hydroxide, and the like, natural or synthetic solid silicates, such as magnesium, aluminium or zinc silicates and the like, kaolin, attapulgite, bentonite, mica and the like, glass fibre, and the like, porous solid silicates (bentonite, attapulgite, and the like) comprising an active material which is stable and insoluble in water under the pH and temperature conditions of the slurry formation operation; mention may be made, as example of active materials, of those possessing biological activity (pharmaceutical, plant-protection, and the like), solid organic polymers, such as polyethylenes, polyesters, and the like, solid non-polymer organic materials, which may or may not be crystalline, possessing biological activity (pharmaceutical, plant-protection, and the like).

The support employed can have any size depending on the desired applications, for example of the order of 20 nm to 30 μm, preferably of the order of 50 nm to 20 μm.

Mention may particularly be made, among the electrolytes, of the salt of the starting silicate metal and of the acidifying agent; it is preferably sodium sulphate; however, sodium chloride, nitrate or hydrogencarbonate may be preferred if the presence of residual sulphate ions is not desired.

The first stage consists in preparing the initial vessel heel.

If the support employed is a solid material, the latter can be introduced as is or, preferably, in the form of an aqueous dispersion. If it is a liquid, the latter is preferably employed in the form of an aqueous emulsion.

The amount of support which can be employed is such that the vessel heel formed contains of the order of at least 10% of its weight of solid support or of the order of at least 10% of its volume of liquid support; the said vessel heel can generally contain up to 50% of its weight or of its volume of solid or liquid support.

A buffer or basic agent can be employed in the initial vessel heel in order to ensure a pH of the said vessel heel of the order of 8 to 10. Mention may be made, as buffer or basic agent, of alkali metal hydroxides, such as sodium hydroxide, dissolved alkali metal silicates, alkali metal phosphates, alkali metal hydrogencarbonates and the like.

The vessel heel obtained is brought to a temperature of the order 80 to 98° C.

The second stage consists in adding the silicate solution and the acidifying agent simultaneously to the vessel heel, which is kept stirring.

The respective amounts of alkali metal silicate and of acidifying agent are chosen so as to obtain the kinetics K of formation of active silica mentioned above and so as to maintain the pH of the reaction mixture at a substantially constant value of the order of 8 to 10 throughout the introduction of the two reactants.

These two solutions are introduced while maintaining the mixture at a temperature of the order of 80 to 98° C.

The introduction of the silicate solution is halted when the desired amount of silica has been formed. The minimum amount of silica desired is that corresponding to a deposition of the order of 1 to 150 parts by weight of $SiO_2$ per 100 parts by weight of support.

This second stage generally lasts of the order of 30 minutes to 2 hours.

The pH of the mixture obtained at the end of the second stage, after halting the introduction of the reactants, is subsequently brought, if necessary, to a value of less than 7, preferably of the order of 4 to 5.

The mixture obtained at the end of the second stage, after halting the introduction of the reactants, is optionally allowed to mature for approximately 10 to 30 minutes under the same temperature conditions. This optional maturing operation can be carried out either before or after having brought the pH of the mixture to a value of less than 7, preferably of the order of 4 to 5, if this pH correction is necessary.

On conclusion of the abovedescribed operations, a silica slurry is obtained, which slurry is subsequently separated (liquid/solid separating); this operation generally consists of a filtration (for example, separating by settling, use of a rotary vacuum filter), followed by washing with water.

The silica suspension thus recovered (filtration cake) is subsequently dried (oven, stove, atomization).

The particles thus obtained can exhibit a dense silica shell thickness of the order of 2 to 200 nm, preferably of the order of 5 to 50 nm, for a support core size of the order of 20 nm to 30 μm, preferably of the order of 50 nm to 20 μm.

The method forming the subject-matter of the invention is well suited to the preparation of dense silica particles exhibiting a shell thickness of the order of 2 to 200 nm, preferably of the order of 5 to 50 nm, for a core size of the order of 20 nm to 30 μm, preferably of the order of 50 nm to 20 μm.

It makes it possible to obtain, according to the desired application, both particles with a dense silica shell which is brittle and easily broken by mechanical action and particles with a dense silica shell which withstands mechanical actions. Particles with a dense silica shell which is mechanically brittle can exhibit a shell thickness of less than approximately 20 nm, preferably of less than approximately 10 nm, in particular if the size of the core is greater than 10 μm, very particularly greater than 15 μm.

These particles generally exhibit a BET surface of the order of 0.1 to 200 $m^2/g$; the latter depends on the initial BET of the support.

The BET specific surface is determined according to the Brunauer-Emmet-Teller method described in "The Journal of the American Chemical Society", Vol. 60, page 309, February 1938, corresponding to NFT Standard 45007 (November 1987).

The thickness of the shell is determined by electron microscopy.

According to an alternative embodiment of the invention, the silica shell of the particles present in the slurry additionally contains traces of polyvalent cations, such as $Mg^{2+}$, $Ca^{2+}$, $Ba^{2+}$ or $Pb^{2+}$, preferably introduced in the aqueous solution form during the slurry formation operation, in the first stage in the vessel heel or, in the second stage, during the simultaneous addition of the reactants.

The presence of traces of polyvalent cations which can be removed in a following stage, for example by the action of an acid (this is the case, in particular, of $Ca^{2+}$, and the like), is very particularly advantageous for introducing microporosity into the dense silica shell. This is because a microporous structure of the dense silica shell is advantageous for a release or an improvement in the release over time of the material constituting the core by diffusion through the dense silica shell.

A second subject-matter of the invention consists, as novel industrial products, of composite particles composed of a precipitated dense silica shell and of a core made of a solid non-polymer organic material, which may or may not be crystalline, which possesses biological activity (pharmaceutical, plant-protection, and the like) and which is insoluble in an aqueous medium with a pH of the order of 8 to 10 at a temperature of less than 100° C.

The said composite particles can preferably be prepared according to the method described above; they can also be obtained by any preparation method which makes possible the deposition of dense silica by precipitation from an alkali metal silicate on a support (for example, according to the method disclosed in U.S. Pat. No. 2,885,366). They can exhibit a dense silica shell thickness of the order of 2 to 200 nm, preferably of the order of 5 to 50 nm, for a support core size, the support possessing biological activity, of the order of 20 nm to 30 µm, preferably of the order of 50 nm to 20 µm. The dense silica shell of the said composite particles can equally well be brittle and easily broken by mechanical action or resistant to mechanical actions.

The particles forming the subject-matter of the invention or obtained according to the method of the invention, composed of a dense silica shell coating a support core, the support being made of a material other than silica, can have multiple applications. Particles which are resistant to mechanical action and with a core composed of a low-cost solid material can be used as filler for rubber or polymers, fillers for concretes or for papers, and the like.

Particles with a shell which is sensitive to mechanical or chemical action can be used, as is or in a solid or liquid formulation, as vehicles for solid active materials or active principles, in particular possessing biological activity (pharmaceutical, plant-protection, and the like), constituting the core or included in the core, with the release of the active material or of the active principle by destruction of the shell by mechanical or chemical action.

Particles resistant to mechanical action can also be used for the delayed release of solid active materials or active principles possessing biological activity, in particular plant-protection activity, constituting the core or included in the core by slow diffusion through the silica shell, it being possible for this diffusion optionally, if desired, to be accelerated by the presence of microporosity in the silica shell.

The following examples are given by way of illustration.

EXAMPLE 1

A vessel heel is prepared by introduction, into a 15 litre reactor, of 5 litres of water, of 0.43 mol/litre of vessel heel of sodium in the sodium sulphate form, of 1500 g of precipitated calcium carbonate (Sturcal H, sold by Rhône-Poulenc, exhibiting a particle size of 11 µm and a BET specific surface of 4 m$^2$/g) and of sodium silicate, with an SiO$_2$/Na$_2$O ratio of 3.5 (aqueous solution containing 130 g of SiO$_2$ per litre), in an amount corresponding to a concentration of 5 g of SiO$_2$ per litre of vessel heel. The vessel heel, with a pH of 8.5, is brought to 90° C. and kept stirring. The following are subsequently simultaneously introduced:

an aqueous sodium silicate solution with an SiO$_2$/Na$_2$O ratio of 3.5, the concentration of which is 130 g of SiO$_2$ per litre of solution, and an aqueous sulphuric acid solution containing 80 g of acid per litre, so as to form 300 g of silica in 50 minutes.

After maturing for about twenty minutes, the slurry obtained is filtered; the filtration cake is washed with water and then dried by atomization.

Analysis of the product by electron microscopy (TEM) shows that the thickness of the silica layer deposited is of the order of 20 nm.

The BET surface of the final particles is 3.2 m$^2$/g.

The kinetics of addition of the sodium silicate was 0.24 g (SiO$_2$)/h/g (CaCO$^3$), against 0.02 g (SiO$_2$)/h/g (CaCO$^3$) according to the prior art (U.S. Pat. No. 2,885,366)

EXAMPLE 2

A vessel heel is prepared by introduction, into a 15 litre reactor, of 5 litres of water, of 0.43 mol/litre of vessel heel of sodium in the sodium sulphate form, of 1150 g of precipitated calcium carbonate (Sturcal H, sold by Rhône-Poulenc, exhibiting a particle size of 11 µm and a BET specific surface of 4 m$^2$/g) and of sodium silicate, with an SiO$_2$/Na$_2$O ratio of 3.5 (aqueous solution containing 130 g of SiO$_2$ per litre), in an amount corresponding to a concentration of 2 g of SiO$_2$ per litre of vessel heel. The vessel heel, with a pH of 9, is brought to 90° C. and kept stirring.

The following are subsequently simultaneously introduced:

an aqueous sodium silicate solution with an SiO$_2$/Na$_2$O ratio of 3.5, the concentration of which is 130 g of SiO$_2$ per litre of solution, and gaseous CO$_2$, so as to form 230 g of silica in 90 minutes.

After maturing for about ten minutes, the slurry obtained is filtered; the suspension cake is washed with water and then dried in an oven at 80° C.

Analysis of the product by electron microscopy (TEM) shows that the thickness of the silica layer deposited is of the order of 20 nm.

The BET [lacuna] surface of the final particles is 3.7 m$^2$/g. The kinetics of addition of the sodium silicate was 0.134 g (SiO$_2$)/h/g (CaCO$_3$), against 0.02 g (SiO$_2$)/h/g (CaCO$_3$) according to the prior art (U.S. Pat. No. 2,885,366).

What is claimed is:

1. A process for the preparation of particles presenting a dense silica shell comprising the steps of:

1) precipitating an active silica from an aqueous alkali metal M silicate solution, with an SiO$_2$/Na$_2$O ratio of at least 2 with adjustment of the pH using an acidifying agent, on a support made of a material other than silica in order to obtain a silica slurry;

2) separating the silica slurry in the form of a silica suspension; and 3) drying said silica suspension, wherein in step 1) the formation of silica slurry by precipitation comprises the following stages:

a first stage comprising employing an initial vessel heel with a pH of about 8 to about 10 comprising water, at least one organic or inorganic support other than silica which is insoluble in water under the conditions of the slurry formation, an electrolyte salt of an alkali metal, the amount of the electrolyte present being at least about 0.4 mol, of alkali metal ion per liter of vessel heel, and optionally a buffer or basic agent, at a temperature of the order of about 80 to about 98° C.; and a second stage comprising introducing, into said vessel heel, the alkali metal silicate in the form of an aqueous solution containing at least about 100 grams of SiO$_2$/liter, and the acidifying agent, to form a reaction mixture under conditions such that the kinetics K of formation of active silica, expressed in grams of silica/hour/gram of support, corresponds to a value:

$$K \geq 3'(A/200)2'',$$

n being equal to (T-90)/10,

A representing the specific surface, expressed in m²/g, of the support to be coated, and T the temperature in °C. of said reaction mixture, the reaction mixture exhibiting a constant pH of about 8 to 10 and being maintained at a temperature T of about 80 to 98° C., until the desired amount of active silica has been formed.

2. A process according to claim 1, wherein in step 1) the $SiO_2/Na_2O$ ratio is of about 2.5 to about 4.

3. A process according to claim 1, wherein in step 1) the amount of electrolyte present is of about 0.4 to about 0.5 mol of alkali metal ion per liter of vessel heel.

4. A process according to claim 1, wherein $K \geq 4$ (A/200) $2^n$.

5. A process according to claim 4, wherein $K \geq 6$ (A/200) $2^n$.

6. A process according to claim 1, wherein the alkali metal silicate is a sodium or potassium silicate.

7. A process according to claim 1, wherein the acidifying agent is an inorganic or organic acid.

8. A process according to claim 7, wherein the acidifying agent is sulphuric, nitric, hydrochloric, acetic, formic or carbonic acid.

9. A process according to claim 1, wherein the acidifying agent is gaseous $CO_2$ or sulphuric acid in the form of an aqueous solution exhibiting a concentration of about 60 to about 400 g/l.

10. A process according to claim 1, wherein the material constituting the support is solid inorganic metal salts, metal powders, solid metal oxides, solid metal hydroxides, natural synthetic solid silicates, synthetic solid silicates, porous solid silicates comprising an active material which is stable and insoluble in water under the pH and temperature conditions of the slurry formation in step 1), solid organic polymers, or solid non-polymer organic materials, optionally crystalline and possessing biological activity.

11. A process according to claim 10, wherein the material constituting the support is calcium carbonate or a solid non-polymer organic materials, optionally crystalline and possessing biological activity.

12. A process according to claim 11, wherein the biological activity is a plant-protection activity.

13. A process according to claim 12, wherein the material constituting the support has any shape and a size of about 20 nm to about 30 μm.

14. A process according to claim 13, wherein the material constituting the support has a size of about 50 nm to about 20 μm.

15. A process according to claim 1, wherein the electrolyte is sodium sulphate, chloride, nitrate or hydrogencarbonate.

16. A process according to claim 1, wherein the support is employed in the form of an aqueous dispersion.

17. A process according to claim 1, wherein the support is present in an amount such that the vessel heel formed contains at least about 10% of its weight or of its volume of support.

18. A process according to claim 17, wherein the vessel heel contains up to 50% of its weight or of its volume of support.

19. A process according to claim 1, wherein the second stage of slurry formation is carried out by simultaneous introduction of the alkali metal silicate and of the acidifying agent, until the formation of at least 1 to 150 parts by weight of $SiO_2$ per 100 parts by weight of support.

20. Composite particles comprising an active silica shell and a core composed of a support made of a material other than silica made by the process of claim 1, and exhibiting a silica shell thickness of about 2 to about 200 nm, for a support core size of about 20 nm to about 30 μm.

21. Composite particles according to claim 20, exhibiting a silica shell thickness of about 5 to about 50 nm, for a support core size of about 50 nm to about 20 μm.

22. Composite particles according to claim 21, wherein they exhibit a silica shell thickness of less than about 20 nm.

23. Composite particles according to claim 22, wherein they exhibit a support core size of greater than about 10 μm.

24. Composite particles composed of a precipitated dense silica shell and of a core made of a solid non-polymer organic material, optionally crystalline and possessing biological activity, said core being insoluble in an aqueous medium having a pH of about 8 to about 10 at a temperature of less than 100° C.

25. Composite particles according to claim 24, exhibiting a silica shell thickness of about 2 to about 200 nm, for a support core size of about 20 nm to about 30 μm.

26. A process for the delayed release of a solid non-polymer organic material possessing biological activity comprising the step of slow diffusing said solid non-polymer organic material of composite particles as defined in claim 25 through the silica shell of said composite particles.

* * * * *